United States Patent
Kuo et al.

(10) Patent No.: US 10,456,153 B2
(45) Date of Patent: Oct. 29, 2019

(54) MEDICAL CLAMPING INSTRUMENT

(71) Applicant: HIWIN TECHNOLOGIES CORP., Taichung (TW)

(72) Inventors: Chin-Hsing Kuo, Taichung (TW); Ting-Hao Liu, Taichung (TW); Ren-Jeng Wang, Taichung (TW)

(73) Assignee: Hiwin Technologies Corp., Taichung (TW)

( * ) Notice: Subject to any disclaimer, the term of this patent is extended or adjusted under 35 U.S.C. 154(b) by 242 days.

(21) Appl. No.: 15/457,241

(22) Filed: Mar. 13, 2017

(65) Prior Publication Data
US 2018/0256182 A1 Sep. 13, 2018

(51) Int. Cl.
*A61B 17/29* (2006.01)

(52) U.S. Cl.
CPC ...... *A61B 17/29* (2013.01); *A61B 2017/2903* (2013.01); *A61B 2017/2927* (2013.01); *A61B 2017/2932* (2013.01); *A61B 2017/2939* (2013.01)

(58) Field of Classification Search
CPC ... A61B 17/28; A61B 17/282; A61B 17/2804; A61B 17/2812; A61B 17/2816; A61B 17/29; A61B 2017/2808; A61B 2017/2908; A61B 2017/2927; A61B 2017/2932; A61B 2017/2939; A61B 2017/294; A61B 2017/2941
USPC ................................................. 606/205–208
See application file for complete search history.

(56) References Cited

U.S. PATENT DOCUMENTS

| | | | |
|---|---|---|---|
| 5,374,277 A * | 12/1994 | Hassler | A61B 17/29 606/170 |
| 6,312,435 B1 | 11/2001 | Wallace et al. | |
| 6,394,998 B1 | 5/2002 | Wallace et al. | |
| 6,676,684 B1 | 1/2004 | Morley et al. | |
| 2007/0162072 A1 | 7/2007 | Nicholas et al. | |
| 2010/0087818 A1 * | 4/2010 | Cunningham | A61B 17/29 606/53 |

* cited by examiner

*Primary Examiner* — Martin T Ton
(74) *Attorney, Agent, or Firm* — Muncy, Geissler, Olds & Lowe, P.C.

(57) ABSTRACT

A medical clamping instrument includes first and second tubular members pivotally connected together, a first rod member pivotally connected to the second tubular member, a second rod member pivotally connected to the first rod member, first and second claw arms respectively providing first and second clamping portions and first and second connecting portions and respectively pivotally connected to the second tubular member, third and fourth rod members respectively pivotally connected to the first and second connecting portions, a screw nut pivotally connected to the third and fourth rod members, a screw rod threaded into the screw nut and driven by a driving rod via the first universal joint, the fifth rod member and the second universal joint. Thus, operating the driving rod can move the first and second clamping portions, maintaining the clamping force stably.

4 Claims, 6 Drawing Sheets

MEDICAL CLAMPING INSTRUMENT

BACKGROUND OF THE INVENTION

1. Field of the Invention

The present invention relates to medical instrument technology and more particularly, to a medical clamping instrument that is capable of maintaining the clamping force stably.

2. Description of the Related Art

With the development of medical technology, minimally invasive surgery has been the trend in major surgery, which does not leave a large wound after surgery, significantly shortening the patient's rehabilitation time. In laparoscopic and endoscopic surgery, a small incision, puncture or intubation is firstly made in the patient's body, allowing the insertion of various surgical instruments such as scissors, dissector or retractor to perform the procedure Various surgical instruments are known, such as U.S. Pat. Nos. 6,312,435, 6,394,998, 6,676,684 and US2007/0162072A1. According to conventional designs, steel wires are commonly used for pulling terminal minimally invasive components to perform the action of clamping, achieving the effect of enabling the end effector to have the characteristics of miniaturization and multi-degree of freedom movement. However, numerous components and complex mechanism are bound to bring the problems of complicated assembly process and a large error in product accuracy. Further, the main problem of using a steel wire to pull a component part is that a steel wire has stretch elasticity and it must be adjusted or even replaced after a long use. Therefore, there is still room for improvement in the clamping force stability of conventional steel wire-driven type medical clamping instruments.

Further, the operating range of a medical clamping instrument is also the design focus of minimally invasive surgical instruments. Since minimally invasive surgery is performed under a narrow operating environment, if the range of motion of the medical clamping instrument is insufficient, it will be necessary to carry out device exchange so as to meet the surgical needs. This will not only lead to increased surgical time and inconvenience, but also make it more likely to increase the risk of surgery. Therefore, while considering the stability of the clamping force, it should also consider the operating range.

SUMMARY OF THE INVENTION

The present invention has been accomplished under the circumstances in view. It is the main object of the present invention to provide a medical clamping instrument that is capable of maintaining the clamping force stably and has a wide operating range.

To achieve this and other objects of the present invention, a medical clamping instrument comprises: a first tubular member; a second tubular member pivotally connected to the first tubular member; a first rod member pivotally connected to the second tubular member; a second rod member inserted into the first tubular member and pivotally connected to the first rod member; a first claw arm having a first clamping portion, a first connecting portion and a middle defined between the first clamping portion and the first connecting portion and pivotally connected to the second tubular member; a second claw arm having a second clamping portion, a second connecting portion and a middle defined between the second clamping portion and the second connecting portion and pivotally connected to the first claw arm or the second tubular member; a third rod member pivotally connected to the first connecting portion; a fourth rod member pivotally connected to the second connecting portion; a screw nut pivotally connected to the third rod member and the fourth rod member; a screw rod threaded into the screw nut; a first universal joint affixed to the screw rod; a fifth rod member affixed to the first universal joint; a second universal joint affixed to the fifth rod member; and a driving rod inserted through the first tubular member and affixed to the second universal joint.

Thus, rotating the driving rod can drive the second universal joint, the fifth rod member and the first universal joint to rotate the screw rod, therefore the screw nut that is threaded onto the screw rod can be driven by the screw rod to move, and at the same time, the third and forth rod members that are pivoted to the screw nut can be forced to move the first and second connecting portions, thereby biasing the first and second clamping portions. Thus, the present invention can maintain the clamping force stably. Further, operating the second rod member and the first rod member can bias the second tubular member and the first and second clamping portions relative to the first tubular member; thus, mating with the linear reciprocating motion of the driving rod relative to the first tubular member, the biasing angle of the second tubular member can be increased, widening the operating range of the medical clamping instrument.

Further, when the second rod member is driven by an external force, it is forced to make an active linear reciprocating motion relative to the first tubular member, causing the second rod member to move the first rod member and to further bias the second tubular member relative to the first tubular member.

Further, when the driving rod is driven by an external force, it is forced to make an active rotary motion and a passive linear reciprocating motion relative to the first tubular member, causing the driving rod to rotate the screw rod, and thus, the screw rod can be moved back and forth linearly by an external force to mate with the basing of the second tubular member, widening the operating range of the medical clamping instrument.

Further, the driving rod can be configured to provide an outer rod member and an inner rod member. The outer rod member is inserted into the first tubular member, comprising an insertion slot and a sliding groove. The inner rod member is inserted into the insertion slot, comprising a protruding portion. The protruding portion is inserted into the sliding groove, and movable with the inner rod member along the sliding groove. Further, the second universal joint can be affixed to the outer rod member or the inner rod member.

Further, in addition to the advantage of increasing the biasing angle of the second tubular member to widen the operating range of the medial clamping instrument, the invention also enables the driving rod to be forced by an external force to make a linear motion smoothly.

Other advantages and features of the present invention will be fully understood by reference to the following specification in conjunction with the accompanying drawings, in which like reference signs denote like components of structure.

DETAILED DESCRIPTION OF THE INVENTION

Figure 1:
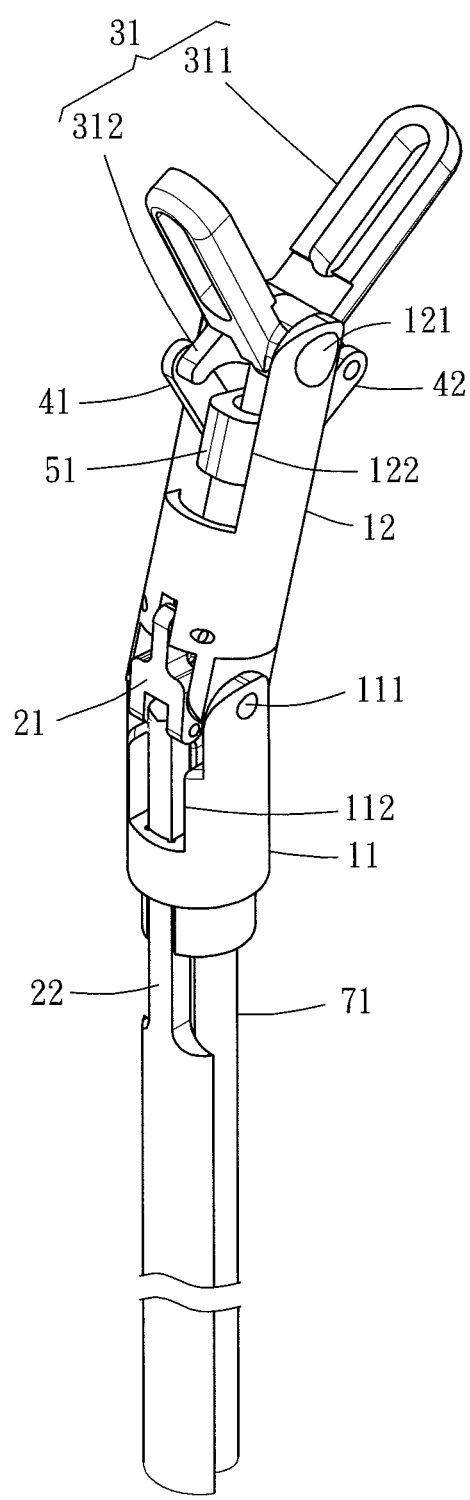
FIG. 1 is an elevational of a medical clamping instrument in accordance with a first embodiment of the present invention.
Figure 2:
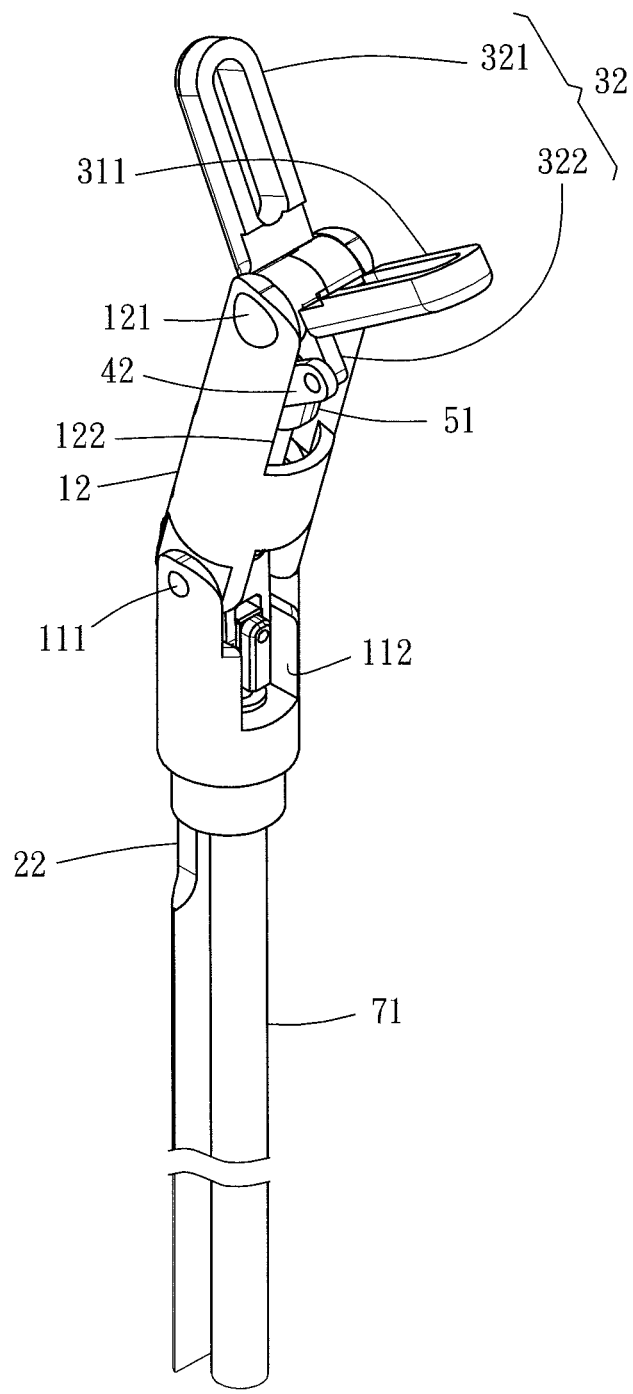
FIG. 2 corresponds to FIG. 1 when viewed from another angle.
Figure 3:
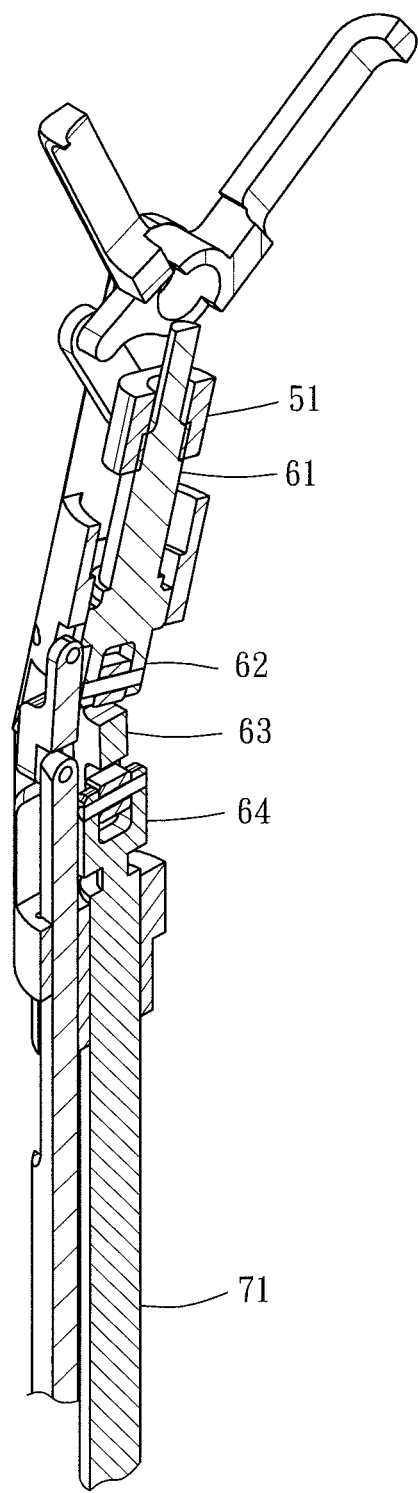
FIG. 3 is a sectional elevation of the medical clamping instrument in accordance with the first embodiment of the present invention.
Figure 4:
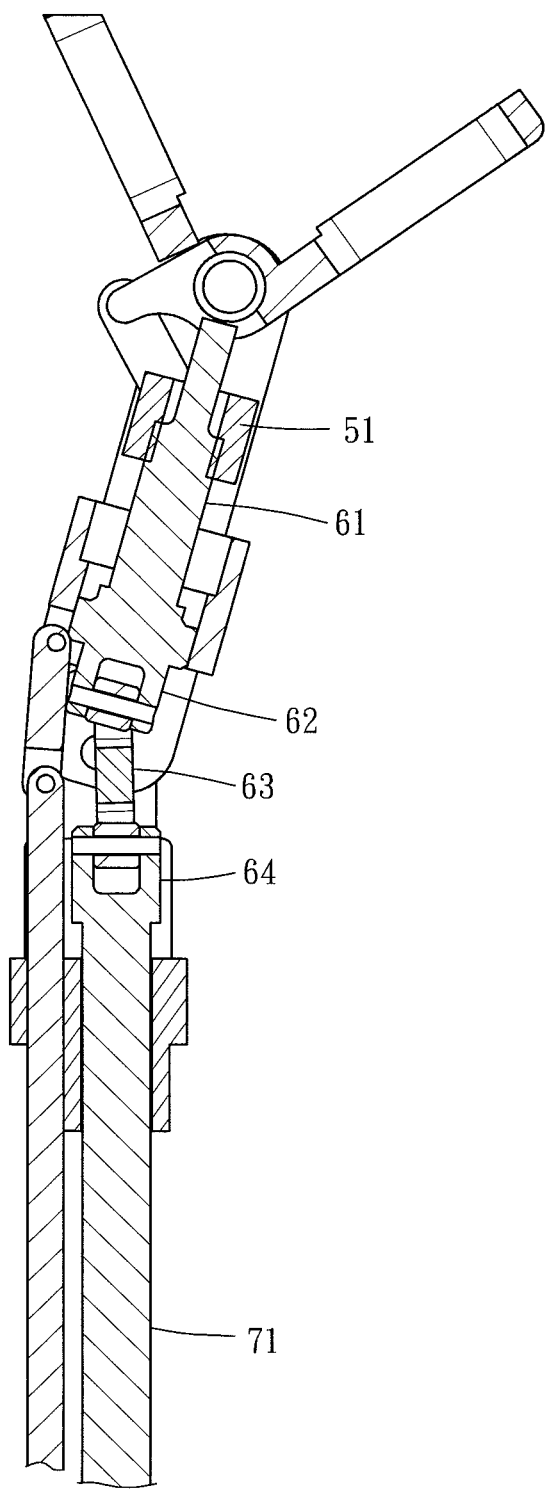
FIG. 4 is a sectional side view of the medical clamping instrument in accordance with the first embodiment of the present invention.

Referring to FIGS. 1-4, a medical clamping instrument in accordance with a first embodiment of the present invention is shown. As illustrated, the medical clamping instrument comprises: a first tubular member 11, a second tubular member 12, a first rod member 21, a second rod member 22, a first claw arm 31, a second claw arm 32, a third rod member 41, a fourth rod member 42, a screw nut 51, a screw rod 61, a first universal joint 62, a fifth rod member 63, a second universal joint 64 and a driving rod 71.

The first tubular member 11 comprises a first connection end 111, and a first accommodation slot 112 axially located on the first connection end 111.

The second tubular member 12 is pivotally connected to the first connection end 111 of the first tubular member 11. The second tubular member 12 comprises a second connection end 121, and a second accommodation slot 122 axially located on the second connection end 121.

The first rod member 21 is pivotally connected to the second tubular member 12.

The second rod member 22 is inserted into the first tubular member 11 and pivotally connected to the first rod member 21. In this embodiment, the second rod member 22 is pivotally connected with the first rod member 21 in the first accommodation slot 112 so that when the user uses the second rod member 22 to bias the first rod member 21 and then the second tubular member 12 relative to the first tubular member 11, the movement of the first rod member 21 and the second rod member 22 becomes free from the interference of the first tubular member 11.

The first claw arm 31 comprises a first clamping portion 311 and a first connecting portion 312 connected together. Further, a part of the first claw arm 31 between the first clamping portion 311 and the first connecting portion 312 is pivotally connected to the second connection end 121 of the second tubular member 12. When the first connecting portion 312 receives an external force, it will drive the first clamping portion 311 to move. It is to be noted that, in this embodiment, the first connecting portion 312 can protrude out of the second accommodation slot 122, so that when the first connecting portion 312 is biased relative to the second connection end 121 of the second tubular member 12, the first connecting portion 312 is free from the interference of the second tubular member 12.

The second claw arm 32 comprises a second clamping portion 321 and a second connecting portion 322 connected together. Further, a part of the second claw arm 32 between the second clamping portion 321 and the second connecting portion 322 is pivotally connected to the first claw arm 31 or the second tubular member 12.

The third rod member 41 is pivotally connected to the first connecting portion 312. The fourth rod member 42 is pivotally connected to the second connecting portion 322. Pulling or pushing the third rod member 41 and the fourth rod member 42 will respectively bias the first connecting portion 312 and the second connecting portion 322 relative to the second connection end 121 of the second tubular member 12.

The screw nut 51 is pivotally connected to the third rod member 41 and the fourth rod member 42.

The screw rod 61 is threaded into the screw nut 51.

The first universal joint 62 is affixed to the screw rod 61. It's worth mentioning that, in this embodiment, the first universal joint 62 and the screw rod 61 are integrally made in one piece, however, this one-piece arrangement is not a limitation.

The fifth rod member 63 is affixed to the first universal joint 62.

The second universal joint 64 is affixed to the fifth rod member 63. It is to be noted that there is a product on the market called "universal joint" that is the combination of the first universal joint 62, the fifth rod member 63 and the second universal joint 64. The operation effect and function of this commercial product are same as the combination structure of the first universal joint 62, the fifth rod member 63 and the second universal joint 64, and therefore, this design should be within the scope of the present preferred embodiment.

The driving rod 71 is inserted into the first tubular member 11 and affixed to the second universal joint 64.

After understanding of the structural details of the first embodiment, the operation of this first embodiment will be outlined hereinafter.

After inserting the first tubular member 11 into the object to be picked up, the user firstly needs to rotate the first tubular member 11 to the desired position in consideration of the expected position of the second tubular member 12. Thereafter, operate the second rod member 22 to drive the first rod member 21, biasing the second tubular member 12 relative to the first tubular member 11 to the desired position.

When a release operation is to be performed, rotate the driving rod 71. At this time, the second universal joint 64, the fifth rod member 63 and the first universal joint 62 are driven to rotate the screw rod 61, causing movement of the screw nut 51 along the screw rod 61 toward the first claw arm 31. When the screw nut 51 is moving toward the first claw arm 31, the screw nut 51 drives the third rod member 41 and the fourth rod member 42 to bias the first connecting portion 312 of the first claw arm 31 and the second connecting portion 322 of the second claw arm 32 in direction away from each other, and also to bias the first clamping portion 311 and the second clamping portion 321 in direction away from each other, thereby releasing the object.

When performing a gripping operation, rotate the driving rod 71. At this time, the second universal joint 64, the fifth rod member 63 and the first universal joint 62 are driven to rotate the screw rod 61, causing movement of the screw nut 51 along the screw rod 61 in direction away from the first claw arm 31. When the screw nut 51 is moving in direction away from the first claw arm 31, the screw nut 51 drives the third rod member 41 and the fourth rod member 42 to bias the first connecting portion 312 and the second connecting portion 322 toward each other, and also to bias the first clamping portion 311 and the second clamping portion 321 toward each other, thereby gripping the object.

As explained above, rotating the driving rod 71 can drive the second universal joint 64, the fifth rod member 63 and the first universal joint 62 to rotate the screw rod 61, therefore the screw nut 51 that is threaded onto the screw rod 61 can be driven by the screw rod 61 to move, and at the same time, the third and forth rod members 41,42 that are pivoted to the screw nut 51 can be forced to move the first and second connecting portions 312,322, thereby biasing the first and second clamping portions 311,321. In this first embodiment, the driving rod 71, the fifth rod member 63, the fourth rod member 42, the third rod member 41, the second rod member 22 and the first rod member 21 are rod members that have a higher rigidity than steel wires, and therefore, the medical clamping instrument of this first embodiment of the present invention can maintain the clamping force stably.

It is to be noted that when the second rod member 22 is driven by an external force, it will make an active linear reciprocating motion relative to the first tubular member 11, causing the first rod member 21 to bias the second tubular member 12 relative to the first tubular member 11. Further, when the driving rod 71 is driven by an external force, it will make an active rotary motion and a passive linear reciprocating motion relative to the first tubular member 11, causing the driving rod 71 to rotate the screw rod 61, and the screw rod 61 can also be moved back and forth linearly by an external force to mate with the basing of the second tubular member 12, widening the operating range of the present invention. The so-called "active" means: directly driven by an external force; the so-called "passive" means: driven by a force-bearing component that is directly driven by an external force.

Figure 5:
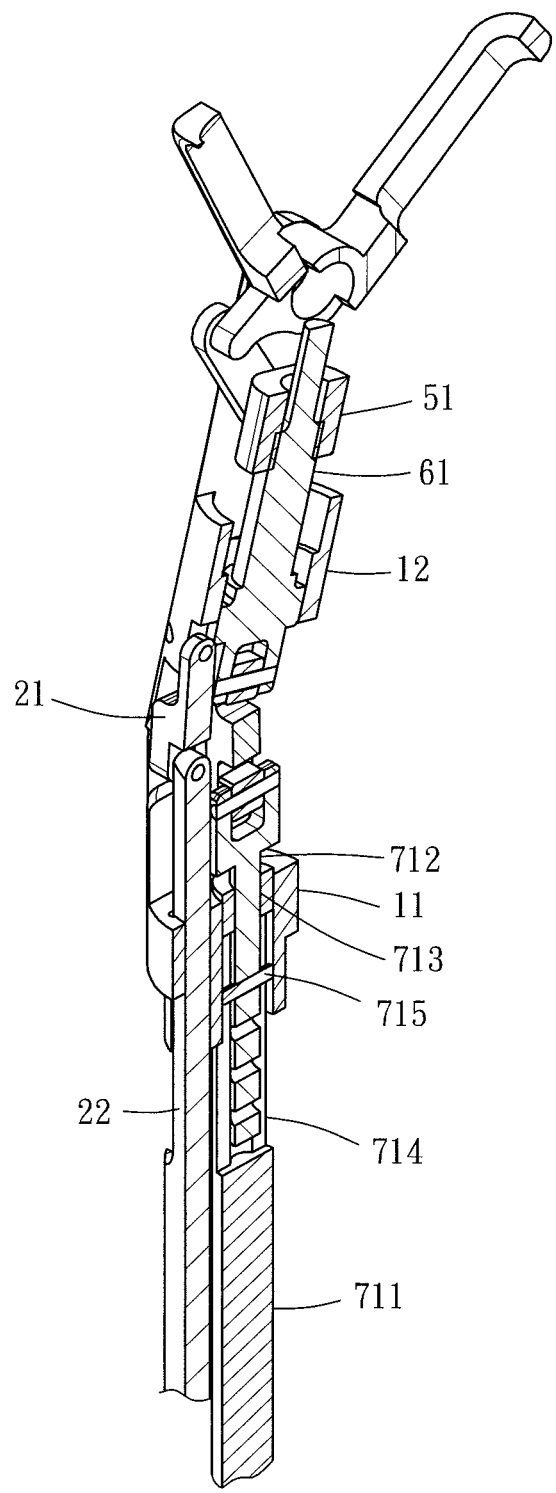
FIG. 5 is a sectional elevation of a medical clamping instrument in accordance with a second embodiment of the present invention.
Figure 6:
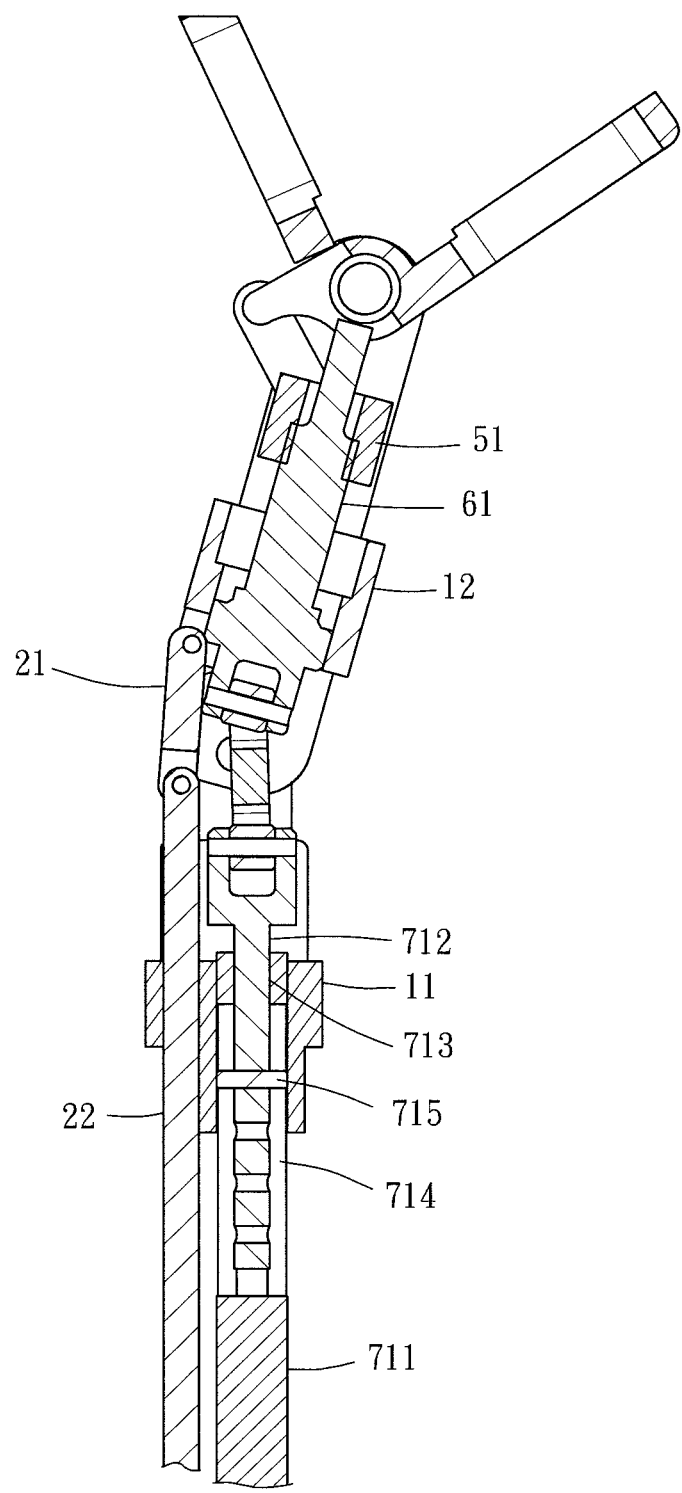
FIG. 6 is a sectional side view of the medical clamping instrument in accordance with the second embodiment of the present invention.

Referring to FIGS. 5 and 6, a medical clamping instrument in accordance with a second embodiment of the present invention is shown. This second embodiment is substantially similar to the aforesaid first embodiment with the exceptions as follows: The driving rod 71 comprises an outer rod member 711 and an inner rod member 712. The outer rod member 711 is inserted into the first tubular member 11, comprising an insertion slot 713 and a sliding groove 714. The inner rod member 712 is inserted into the insertion slot 713, comprising a protruding portion 715. The protruding portion 715 is inserted into the sliding groove 714 and movable with the inner rod member 712 along the sliding groove 714. The second universal joint 64 is affixed to the outer rod member 711 or the inner rod member 712. In this second embodiment, the second universal joint 64 is affixed to the inner rod member 712; however, this second mounting arrangement is not a limitation. Further, the protruding portion 715 in this embodiment is a pin transversely mounted in the inner rod member 712 and partially protruding over the periphery of the inner rod member 712 and inserted into the sliding groove 714.

After explanation of the structural details of this second embodiment, the application of this second embodiment is outlined hereinafter.

When the user pushes or pulls the second rod member 22 to move the first rod member 21 and to further bias the second tubular member 12 to the limitation, the inner rod member 712 will be moved in direction away from the outer rod member 711, thus, the biasing angle of the second tubular member 12 will be larger than that of the aforesaid first embodiment, thereby widening the operating range of the medical clamping instrument. Thus, we can see that when the outer rod member 711 or the inner rod member 712 is driven by an external force, a passive linear reciprocating motion is produced between the outer rod member 711 and the inner rod member 712.

What is claimed is:

1. A medical clamping instrument, comprising:
   a first tubular member;
   a second tubular member pivotally connected to said first tubular member;
   a first rod member pivotally connected to said second tubular member;
   a second rod member inserted into said first tubular member and pivotally connected to said first rod member;
   a first claw arm comprising a first clamping portion and a first connecting portion connected together, and a part defined between said first clamping portion and said first connecting portion and pivotally connected to said second tubular member;
   a second claw arm comprising a second clamping portion and a second connecting portion connected together, and a part defined between said second clamping portion and said second connecting portion and pivotally connected to one of said first claw arm and said second tubular member;
   a third rod member pivotally connected to said first connecting portion;
   a fourth rod member pivotally connected to said second connecting portion;
   a screw nut pivotally connected to said third rod member and said fourth rod member;
   a screw rod threaded into said screw nut;
   a first universal joint affixed to said screw rod;
   a fifth rod member affixed to said first universal joint;
   a second universal joint affixed to said fifth rod member; and
   a driving rod inserted into said first tubular member and affixed to said second universal joint,
   wherein said driving rod comprises an outer rod member and an inner rod member, said outer rod member is inserted into said first tubular member, said outer rod member comprises an insertion slot and a sliding groove, said inner rod member is inserted into said insertion slot and comprises a protruding portion, said protruding portion is inserted into said sliding groove and movable with said inner rod member along said sliding groove; said second universal joint is affixed to one of said outer rod member and said inner rod member.

2. The medical clamping instrument as claimed in claim 1, wherein when said second rod member is driven by an external force, said second rod member is caused to make an active linear reciprocating motion relative to said first tubular member.

3. The medical clamping instrument as claimed in claim 1, wherein when said driving rod is driven by an external force, said driving rod is caused to make an active rotary motion and a passive linear reciprocating motion relative to said first tubular member.

4. The medical clamping instrument as claimed in claim 1, wherein when one of said outer rod member and said inner rod member is driven by an external force, said outer rod member and said inner rod member are caused to make passive linear reciprocating motion relative to each other.

* * * * *